United States Patent [19]

Blattner et al.

[11] 4,235,895
[45] Nov. 25, 1980

[54] SUBSTITUTED 5H-DIBENZ[b,f]AZEPINE

[75] Inventors: Hans Blattner, Riehen; Angelo Storni, Rheinfelden, both of Switzerland

[73] Assignee: Ciba-Geigy Corporation, Ardsley, N.Y.

[21] Appl. No.: 91,274

[22] Filed: Nov. 5, 1979

[30] Foreign Application Priority Data

Nov. 10, 1978 [CH]  Switzerland .................... 1158878

[51] Int. Cl.³ ...................... A61K 31/55; C07D 223/22
[52] U.S. Cl. ................................ 424/244; 260/239 D
[58] Field of Search .................... 260/239 D; 424/244

[56] References Cited

U.S. PATENT DOCUMENTS

| B 520,256 | 1/1976 | Custic et al. | 260/239 D |
|---|---|---|---|
| 2,948,718 | 8/1960 | Schindler | 260/239 D |
| 4,076,812 | 2/1978 | Allgenier et al | 260/239 D |

FOREIGN PATENT DOCUMENTS 375360  4/1964  Switzerland ........................ 260/239 D

*Primary Examiner*—Donald G. Daus
*Assistant Examiner*—M. C. Eakin
*Attorney, Agent, or Firm*—John J. Maitner

[57] ABSTRACT

The substituted 5H-dibenz[b,f]azepine of the formula

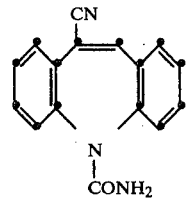

a process for its manufacture, pharmaceutical compositions which contain the novel compound, and a method of treating epilepsy which comprises the use thereof.

3 Claims, No Drawings

SUBSTITUTED 5H-DIBENZ[b,f]AZEPINE

The present invention relates to a novel substituted 5H-dibenz[b,f]azepine, a process for its manufacture, pharmaceutical compositions which contain this compound, and the use thereof.

The novel substituted 5H-dibenz[b,f]azepine of this invention has the formula I

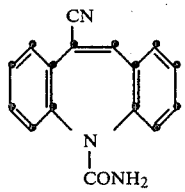
(I)

The novel compound possesses valuable pharmacological properties, in particular an excellent anticonvulsive action. This action is demonstrated in standard test procedures for anticonvulsants, especially in strychnine and picrotoxin antagonism in mice, in the dosage range from about 30 to about 100 mg/kg per os, and from about 60 to about 100 mg/kg per os. These tests were carried out as follows:

Antagonism against picrotoxin-induced spasms

Clonospasms are induced in mice by intraperitoneal injection of 7.5 mg/kg of picrotoxin. The protective action of the test substance, which was administered orally one hour previously, is recorded. Ten test animals are used per dose. One group of animals acts as control. The $ED_{50}$, i.e. the dose at which 50% of the animals are protected, is determined graphically.

Antagonism against lethal spasms induced by strychnine

Lethal spasms are induced in mice by intraperitoneal injection of 2.5 mg/kg of strychnine. The test substance is administered orally one hour beforehand. Ten test animals are used per dose. One group of animals acts as control. The $ED_{50}$, i.e. the dose at which 50% of the animals survive for at least 10 minutes, is determined graphically.

The compound of the formula I is also effective in the electroshock test on mice and rats when administered orally in doses of 6 to 30 mg/kg. The compound of the formula I is also distinguished by low toxicity. In comparison to the pronounced anticonvulsive action, side-effects, such as sedation and muscular hypotonia, are insignificant.

Accordingly, the compound of the formula I can be used for the treatment of epilepsy. It can also be employed as starting material or intermediate for the manufacture of other, especially therapeutically active, compounds.

The compound of the formula I is obtained by methods which are known per se. Thus it is possible to react a compound of the formula

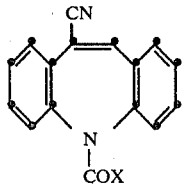
(II)

in which X is halogen having an atomic number of at least 17, with ammonia or ammonia donors. Halogen is accordingly bromine or iodine, but especially chlorine.

The reaction is preferably carried out in an organic solvent, e.g. in a lower alkanol, such as ethanol, isopropanol or butanol, in an ethereal liquid, such as tetrahydrofurane or dioxan, or a hydrocarbon, such as benzene or toluene, at room temperature or preferably at elevated temperature, e.g. at the boiling temperature of the solvent employed. The ammonia can be introduced in gaseous form at the start of the reaction, or during the entire reaction course, or it can also be employed in the form of a concentrated aqueous solution when using a water-miscible solvent. It is, however, also possible to use liquid ammonia and to carry out the reaction, if necessary, in a closed vessel. A particularly suitable ammonia donor is hexamethylenetriamine.

Starting materials of the formula II can be obtained e.g. by reaction of 10-bromo-5H-dibenz[b,f]azepine, which is optionally acylated in the 5-position, with copper(I) cyanide, and subsequent formation of the corresponding carbonyl halide by reaction of the resultant cyano-5H-dibenz[b,f]azepine, optionally accompanied by removal of the 5-acyl radical, with a dihalide of carbonic acid, e.g. phosgene.

The novel compound of the formula I can be used e.g. in the form of pharmaceutical preparations which contain a therapeutically effective amount of the active ingredient, optionally together with inorganic or organic, solid or liquid, pharmaceutically useful carriers, and which are suitable for enteral, e.g. oral, or parenteral administration.

Tablets or gelatin capsules are therefore used which contain the active ingredient together with diluents, for example lactose, dextrose, saccharose, mannitol, sorbitol, cellulose and/or glycine, and/or lubricants, for example silica, talc, stearic acid or salts thereof, such as magnesium or calcium stearate, and/or polyethylene glycol. Tablets can also contain binding agents, for example magnesium aluminium silicate, starches, such as corn, wheat, rice or arrow root starch, gelatin, tragacanth, methyl cellulose, sodium carboxymethyl cellulose and/or polyvinylpyrrolidone, and, if desired, disintegrators, for example starches, agar, aliginic acid or a salt thereof, such as sodium alginate, and/or effervescent mixtures, or adsorption agents, colourants, flavouring matters and sweeteners. It is also possible to use the novel compound of the formula I in the form of preparations which can be administered parenterally, or of infusion solutions. Such solutions are preferably isotonic aqueous solutions or suspensions which can be prepared before use, for example from lyophilised preparations that contain the active ingredient alone or together with a carrier, for example mannitol.

The pharmaceutical preparations, can be sterilised and/or contain adjuvants, for example preservatives, stabilisers, wetting agents and/or emulsifiers, solubility promoters, salts for regulating the osmotic pressure and/or buffers. The pharmaceutical preparations of the invention, which if desired, can contain further pharmacologically useful substances, are manufactured in known manner, for example using conventional mixing, granulating, confectioning, dissolving or lyophilising methods, and they contain from about 0.1% to 100%, especially from about 1% to about 50%, (lyophilisates up to 100%) of the active ingredient.

The invention also relates to the use of the compound of the formula I, preferably in the form of pharmaceutical preparations. The dosage can be dependent on different factors, such as mode of application, species, age and/or the individual condition of the patient. The daily doses for oral application are in the range from about 1 to about 20 mg/kg, and for warm-blooded animals having a body weight of about 70 kg preferably from about 100 mg to about 800 mg.

The invention is illustrated by the following Examples.

EXAMPLE 1

With stirring, 21.8 g (0.1 mole) of 10-cyano-5H-dibenz[b,f]azepine are added to a solution of 19.8 g (0.2 mole) of phosgene in 700 ml of absolute toluene. The mixture is then stirred for 30 hours at 50°–53° C. and subsequently completely concentrated in a rotary evaporator, affording as residue crude 10-cyano-5H-dibenz[b,f]azepine-5-carbonyl chloride with a melting point of 148°–153° C. With stirring, the crude product is dissolved at 70° C. in 600 ml of absolute ethanol. Ammonia gas is then introduced into this solution in the course of 2 hours while constantly keeping the reaction mixture under reflux. The reaction mixture is then concentrated in a rotary evaporator and the residue is washed and dried. Recrystallisation from toluene yields 10-cyano-5H-dibenz[b,f]azepine-5-carboxamide with a melting point of 212°–215° C.

The starting material can be obtained as follows: With stirring, 27.2 g (0.1 mole) of 10-bromo-5H-dibenz[b,f]azepine, 10.7 g (0.12 mole) of copper(I) cyanide and 50 ml of dimethyl formamide are heated at a bath temperature of 150° C. for 1½ hours. The reaction mixture is then cooled to 40° C. and stirred vigorously for 2 hours with 200 ml of a 50% aqueous ethylenediamine solution and 200 ml of methylene chloride. The organic phase is then separated and the aqueous phase is extracted twice with 100 ml of methylene chloride. The combined organic solutions are washed with water, dried over sodium sulfate and concentrated. The residue, consisting of 10-cyano-5H-dibenz[b,f]azepine, is recrystallised from ethanol. Melting point: 143°–145° C.

EXAMPLE 2

Tablets containing 50 mg of 10-cyano-5H-dibenz[b,f]azepine-5-carboxamide can be prepared as follows:

| Composition (10,000 tablets) | |
| --- | --- |
| 10-cyano-5H-dibenz[b,f]azepine-5-carboxamide | 500.0 g |
| lactose | 500.0 g |
| potato starch | 352.0 g |
| gelatin | 8.0 g |
| talc | 60.0 g |
| magnesium stearate | 10.0 g |
| highly disperse silica | 20.0 g |
| ethanol | q.s. |

The 10-cyano-5H-dibenz[b,f]azepine-5-carboxamide is mixed is moistened with an alcoholic solution of the gelatin and granulated through a sieve. After drying, the remainder of the potato starch, the talc, magnesium stearate and the highly disperse silica are admixed and the mixture is compressed to tablets each weighing 145.0 mg and containing 50.0 mg of active ingredient. If desired, these tablets can be provided with a breaking notch for a finer adjustment of the dose.

EXAMPLE 3

Shellac coated tablets containing 100 mg of 10-cyano-5H-dibenz[b,f]azepine-5-carboxamide can be prepared as follows:

| Composition (for 1000 tablets | |
| --- | --- |
| 10-cyano-5H-dibenz[b,f]azepine-5-carboxamide | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| methylene chloride | q.s. |

The 10-cyano-5H-dibenz[b,f]azepine-5-carboxamide, lactose, and 40 g of the corn starch are mixed and the mixture is moistened with a starch paste prepared from 15 g of corn starch and water (with heating) and granulated. The granulate is dried and the remainder of the corn starch, the talc and the calcium stearate are added to and mixed with the granulate. The mixture is compressed to tablets weighing 280 mg and these are then coated with a solution of the hydroxypropylmethylcellulose and the shellac in methylene chloride. Final weight of the coated tablets: 283 mg.

What is claimed is:

1. 10-Cyano-5H-dibenz[b,f]azepine-5-carboxamide of the formula

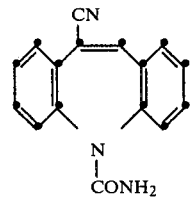

2. A pharmaceutical composition useful in the treatment of epilepsy in a warm-blooded animal comprising a therapeutically effective amount of the compound according to claim 1 and a pharmaceutical carrier.

3. A method of treating epilepsy in a warm-blooded animal which comprises administering to said animal a therapeutically effective amount of the compound according to claim 1.